US009986768B2

(12) United States Patent
Force (10) Patent No.: US 9,986,768 B2
(45) Date of Patent: Jun. 5, 2018

(54) MULTI-PART ELECTRICALLY HEATED AEROSOL-GENERATING SYSTEM

(71) Applicant: Altria Client Services LLC, Richmond, VA (US)

(72) Inventor: Eric Force, Bevaix (CH)

(73) Assignee: ALTRIA CLIENT SERVICES LLC, Richmond, VA (US)

(*) Notice: Subject to any disclaimer, the term of this patent is extended or adjusted under 35 U.S.C. 154(b) by 0 days. days.

(21) Appl. No.: 15/393,605

(22) Filed: Dec. 29, 2016

(65) Prior Publication Data

US 2017/0188633 A1    Jul. 6, 2017

Related U.S. Application Data

(63) Continuation of application No. PCT/EP2016/082435, filed on Dec. 22, 2016.

(30) Foreign Application Priority Data

Dec. 31, 2015   (EP) ..................................... 15203250

(51) Int. Cl.
*A24F 47/00*    (2006.01)
*H05B 1/02*     (2006.01)
(Continued)

(52) U.S. Cl.
CPC ......... *A24F 47/008* (2013.01); *H05B 1/0244* (2013.01); *A61M 5/00* (2013.01); *A61M 11/00* (2013.01); *H05B 2203/021* (2013.01)

(58) Field of Classification Search
CPC ........... A61M 11/042; A61M 2005/006; A24F 47/008
See application file for complete search history.

(56) References Cited

U.S. PATENT DOCUMENTS

2011/0277760 A1   11/2011  Terry et al.
2015/0114409 A1    4/2015  Brammer et al.

FOREIGN PATENT DOCUMENTS

CN     104738816 A    7/2015
EP        2915443     9/2015
GB     2502054 A     11/2013

OTHER PUBLICATIONS

Extended European Search Report for European Patent Application No. 15203250.4 dated Jun. 24, 2016.

(Continued)

*Primary Examiner* — James Harvey
(74) *Attorney, Agent, or Firm* — Harness, Dickey & Pierce, P.L.C.

(57) ABSTRACT

A multi-part aerosol-generating assembly system has a mouth end and a distal end, and includes a first part having a housing and a power supply disposed in the housing. The system also includes a second part releasably connectable with the first part. The second part includes a heating element and a liquid transfer element. The heating element is operably coupled to the power supply when the second part is connected with the first part. The system further includes a third part releasably connectable with the second part. The third part includes a reservoir containing a liquid aerosol generating substrate. The liquid aerosol generating substrate is in fluid communication with the liquid transfer element when the third part is connected with the second part. The system further includes a cover disposable over the third part. The cover is releasably securable in a position relative to the third part.

15 Claims, 8 Drawing Sheets

(51) Int. Cl.
A61M 11/00 (2006.01)
A61M 5/00 (2006.01)

(56) References Cited

OTHER PUBLICATIONS

International Search Report for International application No. PCT/EP2016/082435 dated Mar. 13, 2017.
International Written Opinion for International Application No. PCT/EP2016/082435 dated Nov. 22, 2017.

MULTI-PART ELECTRICALLY HEATED AEROSOL-GENERATING SYSTEM

This is a continuation of and claims priority to PCT/EP2016/082435 filed on Dec. 22, 2016, and further claims priority to EP 15203250.4 filed on Dec. 31, 2015; both of which are hereby incorporated by reference in their entirety.

BACKGROUND

At least one example embodiment relates to multi-part electrically heated aerosol-generating systems for generating an aerosol and associated devices, articles and methods.

One type of aerosol-generating system is an electrically operated handheld aerosol-generating system. Handheld electrically operated aerosol-generating systems include a device portion comprising a battery and control electronics, and a replaceable cartridge portion comprising a supply of aerosol-forming substrate, and an electrically operated vaporizer. A cartridge comprising both a supply of aerosol-generating substrate and a vaporizer is sometimes referred to as a "cartomizer". The vaporizer may comprise a coil of heater wire wound around an elongate wick soaked in liquid aerosol-generating substrate. The cartridge portion may also form a mouthpiece, on which an adult vaper may draw.

However, cartridges having this arrangement may be expensive to produce. In part, a factor may be the cost of manufacturing the wick and coil assembly as well as the mouthpiece portion.

It would be desirable to provide a multi-part aerosol-generating system, such as a handheld electrically operated system, having consumable elements which may be inexpensive to produce.

SUMMARY

In at least one example embodiment, a multi-part aerosol-generating system has a mouth end and a distal end. The system comprises a first part, a second part releasably connectable to the first part, a third part releasably connectable to the second part, and a cover disposable over at least the third part. The first part comprises a housing and a power supply disposed in the housing. The second part comprises a heating element and liquid transfer element. The heating element is electrically connectable to the power supply when the second part is connected with the first part. The third part comprises a reservoir containing a liquid aerosol-generating substrate. The liquid aerosol-generating substrate is in fluid communication with the liquid transfer element when the third part is connected with the second part. The cover is releasably securable in a position relative to the third part and defines the mouth end of the system.

The third part comprising the liquid aerosol-generating substrate may be designed for one-time use. The second part comprising the heating element and the transfer element may be used multiple times. In at least one example embodiment, the liquid reservoir is not refillable by an adult vaper. By providing separate second and third parts, the heating element and the transfer element need not be discarded or replaced every time the liquid aerosol-generating substrate is depleted. In addition, the manufacture of the one-time use aerosol-generating substrate-containing part can be substantially simplified by not including the heating element and the transfer element.

In at least one example embodiment, the provision of a separate cover disposable over, and securable in position relative to, the aerosol-generating substrate-containing third part may allow for simplified or reduced cost of manufacture of the aerosol-generating substrate-containing part relative to a system in which the liquid-containing portion includes a mouthpiece portion.

In at least one example embodiment, the system may provide for a choice of covers or mouthpieces to suit an adult vaper's aesthetic tastes. This may allow for manufacture of a standard format liquid aerosol-generating substrate-containing third part, which standardization can further reduce manufacturing costs, while still providing opportunity for variation with respect to the cover. The cover may also serve the function of providing an additional separation of the adult vaper from to the liquid aerosol-generating substrate, air flow or heater element during use of the system.

At least one example embodiment relates to systems, articles and assemblies that use electrical energy to heat a substrate, without combusting the substrate, to form an aerosol that may be inhaled by an adult vaper. The systems are sufficiently compact to be considered hand-held systems. In at least one example embodiment, the system may be a smoking article. As used herein, the term "smoking article" refers to an article that can deliver a nicotine-containing aerosol for inhalation by an adult vaper.

The term "aerosol generating" article, system or assembly refers to an article, system or assembly comprising an aerosol generating substrate that releases volatile compounds to form an aerosol that may be inhaled by an adult vaper. The term "aerosol generating substrate" refers to a substrate that releases, upon heating, volatile compounds, which may form an aerosol.

Any suitable aerosol generating substrate may be used with the systems. Suitable aerosol generating substrates may comprise plant-based material. In at least one example embodiment, an aerosol generating substrate may comprise tobacco or a tobacco-containing material containing volatile tobacco flavor compounds, which are released from the aerosol generating substrate upon heating. In at least one example embodiment, an aerosol generating substrate may comprise a non-tobacco containing material. An aerosol generating substrate may comprise homogenized plant-based material. An aerosol generating substrate may comprise at least one aerosol former. An aerosol generating substrate may comprise other additives and ingredients such as flavorants. In at least one example embodiment, an aerosol generating substrate comprises nicotine. In at least one example embodiment, an aerosol generating substrate is liquid at room temperature. For example, an aerosol forming substrate may be a liquid solution, suspension, dispersion or the like. In at least one example embodiment, an aerosol generating substrate comprises glycerol, propylene glycol, water, nicotine and, optionally, one or more flavorant.

In at least one example embodiment, the aerosol generating substrate is stored in the third part of a system. The third part comprises a reservoir that contains the aerosol generating substrate. The term "third part" is used interchangeably with "capsule" in the present disclosure.

The third part, or capsule, comprises a housing defining the reservoir. In at least one example embodiment, the housing is a rigid housing. As used herein "rigid housing" means a housing that is self-supporting. The housing may be formed of any suitable material or combination of materials, such as a polymeric material or a metallic material, or a glass. In at least one example embodiment, the housing of the third part is formed by a thermoplastic material. Any suitable thermoplastic material may be used. One suitable thermoplastic material is acrylonitrile butadiene styrene. In at least one example embodiment, the material forming the housing is compatible with the aerosol generating substrate. However, incompatible material may be used if the surface of the housing that forms the reservoir is suitably treated or coated to be compatible with the aerosol generating substrate.

In at least one example embodiment, the distal end portion of the third part comprises an opening in communication with the reservoir through which the aerosol generating substrate may be introduced into the reservoir or removed, such as by flowing, from the reservoir. The terms "distal," "upstream," "proximal," and "downstream" are used to describe the relative positions of components, or portions of components, of an aerosol-generating system. Aerosol-generating systems have a proximal end through which, in use, an aerosol exits the system for delivery to an adult vaper, and have an opposing distal end. The proximal end of the aerosol generating article may also be referred to as the mouth end. An adult vaper may draw on the proximal end of the aerosol generating article in order to inhale an aerosol generated by the aerosol generating article. The terms upstream and downstream are relative to the direction of aerosol movement through the aerosol generating article when an adult vaper draws on the proximal end.

The capsule may comprise a valve positioned relative to the opening to prevent the aerosol generating material from exiting the reservoir when the capsule is not connected to the second part. The valve may be actuatable such that the act of connecting the capsule to the second part causes the valve to open and disconnecting the capsule from the second part causes the valve to close. Any suitable valve may be used. One suitable valve is described in Chinese Patent Application Publication No. CN 104738816 A, which describes a rotary valve assembly. In the rotary valve assembly, a rotatable valve including a liquid outlet is arranged at an outlet end of a liquid storage element. A connection element is provided which can be arranged in the liquid outlet of the valve. Rotation of the connection element on connection of the liquid storage element effects rotation of the valve to align the liquid outlet of the valve with an outlet of a liquid reservoir to allow passage of the liquid from the reservoir to a liquid inlet associated with a heater element. When the liquid storage element is removed, rotation of the connection element rotates the valve back to seal the liquid outlet of the reservoir.

The capsule may comprise a liquid transfer material. A "liquid transfer material" is a material that actively conveys liquid from one end of the material to another, for example by capillary action. The liquid transfer material may be oriented to convey liquid from the reservoir to the second part when the capsule and the second part are connected. In at least one example embodiment, the liquid transfer material may be positioned across the opening exterior to the reservoir. In at least one example embodiment, liquid transfer material or liquid storage material may be contained in the reservoir. In at least one example embodiment, the capsule does not include any liquid transfer material or liquid storage material. In at least one example embodiment, the liquid in the reservoir is present as free liquid and when connected to the second portion is in direct communication with the liquid transfer element of the second part.

Liquid transfer material may have a fibrous or spongy structure. In at least one example embodiment, liquid transfer material includes a web, mat or bundle of fibres. The fibers may be generally aligned to convey the liquid in the aligned direction. The liquid transfer material may comprise sponge-like or foam-like material. The liquid transfer material may comprise any suitable material or combination of materials. Examples of suitable materials are a sponge or foam material, ceramic- or graphite-based materials in the form of fibers or sintered powders, or a fibrous material, for example made of spun or extruded fibers, ceramic or glass.

The capsule is releasably connectable to the second part. As used herein, "releasably connectable" means that the releasably connectable parts may be connected to, and disconnected from each other, without significantly damaging either part. The capsule may be connected to the second part in any suitable manner, such as threaded engagement, snap-fit engagement, interference-fit engagement, magnetic engagement, or the like.

The second part, or "vaporizing unit," comprises a housing, a heating element disposed in the housing, and a liquid transfer element disposed in the housing. The vaporizing unit may include an element that interacts with the valve of the capsule to open the valve and place the liquid transfer material in fluid communication with the reservoir when the capsule is connected to the vaporizing unit. In at least one example embodiment, the liquid in the reservoir is directly transferred to the liquid transfer material of the heater element.

Any suitable liquid transfer material may be used. In at least one example embodiment, the liquid transfer material may comprise a material as previously discussed in relation to the capsule except that the liquid transfer material is suitable for contact with the heating element. In at least one example embodiment, the liquid transfer material may comprise a glass or ceramic material, for example fused silica.

At least a portion of the liquid transfer element is located sufficiently close to the heating element so that liquid aerosol generating substrate carried by the liquid transfer material may be heated by the heating element to generate an aerosol. In at least one example embodiment, the liquid transfer element is in contact with the heating element.

Any suitable heating element may be employed. For example, the heating element may comprise a resistive filament. The term "filament" is used throughout the specification to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner. One or more resistive filament may form a coil, mesh, array, fabric or the like. Application of an electric current to the heating element results in heating due to the resistive nature of the element. In at least one example embodiment, the heating element forms a coil that is wrapped around a portion of the liquid transfer element.

A heating element may comprise any suitable electrically resistive filament. In at least one example embodiment, a heating element may comprise nickel-chromium alloy.

In at least one example embodiment, the housing of the vaporizing unit is a rigid housing. In at least one example embodiment, at least a portion of the housing comprises a thermoplastic material, a metallic material, or a thermoplastic material and a metallic material. In at least one example embodiment, the housing comprises material that efficiently conducts thermal energy and thus can act as a heat sink for the vaporizing unit.

The housing may define one or more air inlets to allow air to be drawn into the vaporizing unit to entrain aerosol resulting from the heating of the aerosol generating substrate. The aerosol may then be guided along the capsule or through a passage in the capsule to the mouth end of the device.

The vaporizing unit may comprise electrical contacts exterior to, or exposed through, the housing for electrically coupling the heating element to the power supply or other control electronics in the first part. In at least one example embodiment, the contacts are exposed at a distal end portion, such as the distal face of the vaporizing unit for operable connection to the first part of the system. In at least one example embodiment, the housing of the vaporizing unit effectively forms the contacts. The heating element may be electrically coupled to the contacts by any suitable electrical conductor. The contacts may be for formed of any suitable electrically conductive material. In at least one example embodiment, the contacts may comprise nickel- or chromium-plated brass.

The vaporizing unit is releasably connectable with the first part. The vaporizing unit may be connected to the second part in any suitable manner, such as threaded engagement, snap-fit engagement, interference-fit engagement, magnetic engagement, or the like.

The first part comprises a housing and power supply disposed in the housing. The first part may also comprise electronic circuitry disposed in the housing and electrically coupled to the power supply. First part may comprise contacts exterior to, or exposed through, the housing such that the contacts of the first part electrically couple with the contacts of the vaporizing unit when the first part is connected with the vaporizing unit. In at least one example embodiment, the contacts are exposed at a proximal end portion, such as the proximal face of the first part for operable connection to the vaporizing unit. In at least one example embodiment, the housing of the first part effectively forms the contacts. The contacts of the first part are electrically coupled to the electronic circuitry and power supply. Thus, when the first part is connected to the vaporizing unit, the heating element is electrically coupled to the power supply and circuitry of the first part.

In at least one example embodiment, the electronic circuitry is configured to control delivery of an aerosol resulting from heating of the substrate to the adult vaper. Control electronic circuitry can be provided in any suitable form and may, for example, include a controller or a memory and a controller. The controller can include one or more of an Application Specific Integrated Circuit (ASIC) state machine, a digital signal processor, a gate array, a microprocessor, or equivalent discrete or integrated logic circuitry. Control electronic circuitry can include memory that contains instructions that cause one or more components of the circuitry to carry out a function or aspect of the control circuitry. Functions attributable to control circuitry in this disclosure can be embodied as one or more of software, firmware, and hardware.

The electronic circuitry may be configured to monitor the electrical resistance of the heater element or of one or more filaments of the heater heating element, and to control the supply of power to the heating element dependent on the electrical resistance of the heating element or the one or more filaments.

The electronic circuitry may comprise a microprocessor, which may be a programmable microprocessor. The electronic circuitry may be configured to regulate a supply of power. Power may be supplied continuously following activation of the system or may be supplied intermittently, such as on a puff-by-puff basis. The power may be supplied to the heater assembly in the form of pulses of electrical current.

The first part may include a switch to activate the system. In at least one example embodiment, the first part may include a button that can be depressed to activate or optionally deactivate the system.

The power supply is typically a battery, but may be or include another form of charge storage device such as a capacitor.

The housing of the first part is a rigid housing. Any suitable material or combination of materials may be used for forming the rigid housing. Examples of suitable materials include metals, alloys, plastics or composite materials containing one or more of those materials, or thermoplastics for example polypropylene, polyetheretherketone (PEEK), acrylonitrile butadiene styrene and polyethylene.

In at least one example embodiment, an aerosol-generating system includes a cover that is disposable over at least the capsule. In at least one example embodiment, the cover includes a distal end opening that is configured to receive the capsule. The cover may also extend over at least a portion of the vaporizing unit, and may extend over at least a portion of the first part. In at least one example embodiment, the cover extends over the capsule and the vaporizing unit and abuts a proximal end of the first part. Having the cover extend over the vaporizing unit may be beneficial because the vaporizing unit may be replaced from time-to-time. Accordingly, manufacture of vaporizing unit may be standardized, while still providing opportunity for variation with respect to the cover. The cover may extend over the capsule and abut a proximal end of the vaporizing unit. The cover is releasably securable in a position relative to at least the capsule. The cover may be releasably connectable to the first part, the second part, or the third part to be retained in a position relative to the capsule. The cover may be connected to the first, second or third part in any suitable manner, such as threaded engagement, snap-fit engagement, interference-fit engagement, magnetic engagement, or the like. An interior surface of the cover may include one or more resilient members for example resilient fingers for example for providing a friction fit of the cover with other parts of the device. The resilient members may include one or more protrusions or formations for interference fit with one or more portions of other parts of the device.

If the cover extends over the vaporizing unit, a sidewall of the cover may define one or more air inlets to allow air to enter the vaporizing unit.

The cover defines the mouth end of the aerosol-generating system. In at least one example embodiment, the cover is generally cylindrical and tapers inwardly towards the mouth end. The cover comprises a single part. The cover may include a distal part and a releasable connectable proximal part that may serve as a mouthpiece. The cover defines a mouth end opening to allow aerosol resulting from heating of the aerosol-generating substrate to exit the device. The cover may comprise a seal to prevent air other than air containing aerosol from exiting the mouth end of the device.

In at least one example embodiment, the cover comprises an elongate housing. The cover may be substantially rigid. The cover may comprise any suitable material or combination of materials. Examples of suitable materials include metals, alloys, plastics, ceramic, glass or composite materials containing one or more of those materials, for example polypropylene, polyetheretherketone (PEEK) and polyethylene.

In at least one example embodiment, an aerosol-generating system, when all parts are connected, may have any suitable size. In at least one example embodiment, the system may have a length ranging from about 50 mm to about 200 mm. In at least one example embodiment, the system has a length ranging from about 100 mm to about 190 mm. In at least one example embodiment, the system has a length ranging from about 140 mm to about 170 mm.

BRIEF DESCRIPTION OF THE DRAWINGS

Reference will now be made to the drawings. It will be understood that other features not depicted in the drawings fall within the scope and spirit of this disclosure. Like numbers used in the figures refer to like components, steps and the like. It will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

The schematic drawings are not necessarily to scale and are presented for purposes of illustration and not limitation.

DETAILED DESCRIPTION

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments, various features will be described in detail with reference to the attached drawings. However, example embodiments described are not limited thereto.

Figure 1A:
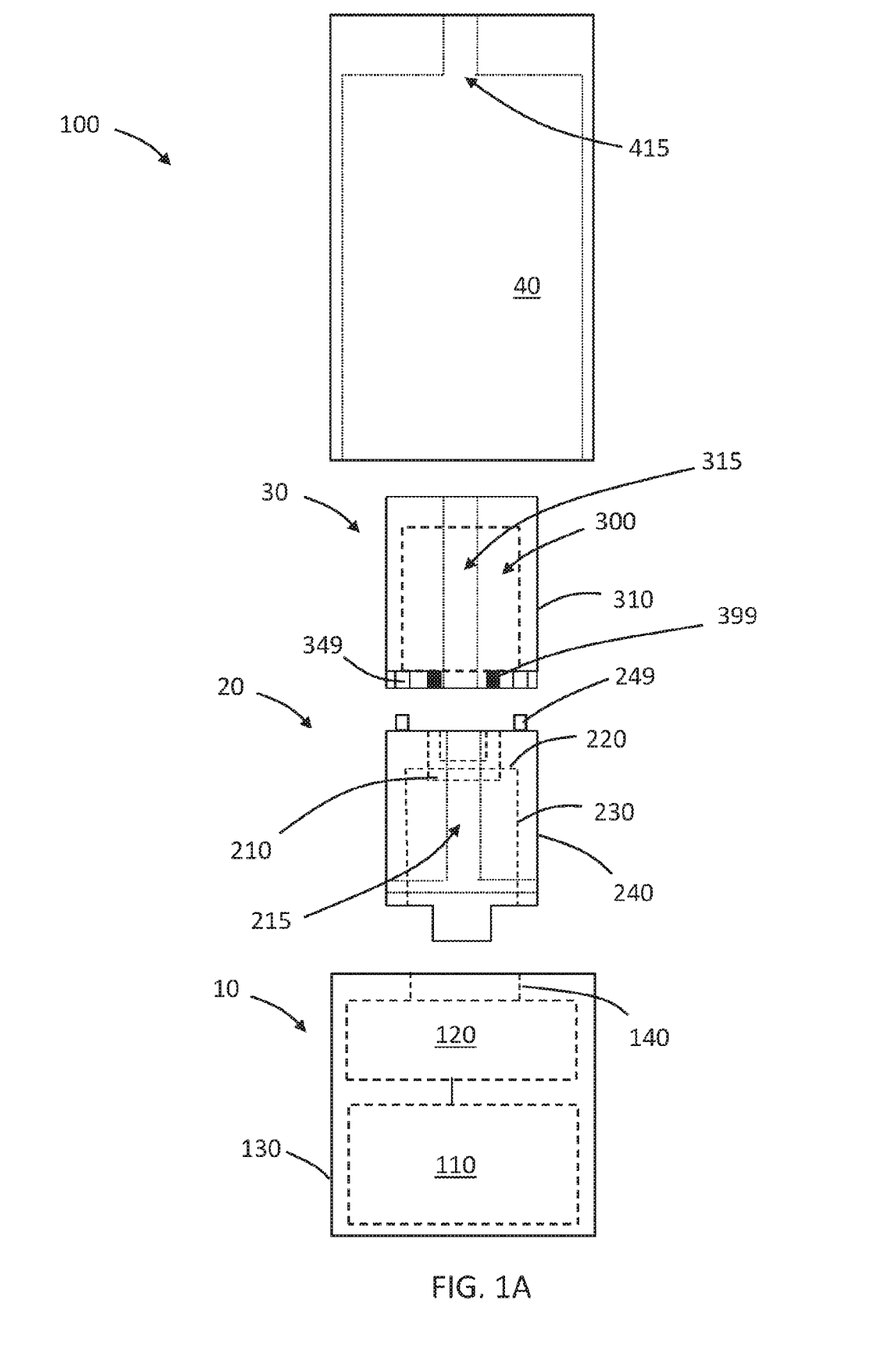
FIG. 1A is a plan view of disconnected first, second and third parts and cover, and illustrates some internal components of the parts.
Figure 1B:
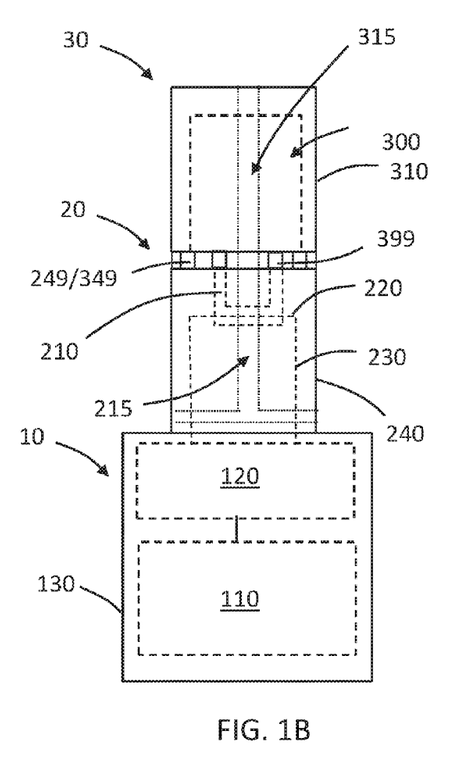
FIG. 1B is a plan view of connected first, second and third parts illustrating some internal components of the parts.
Figure 1C:
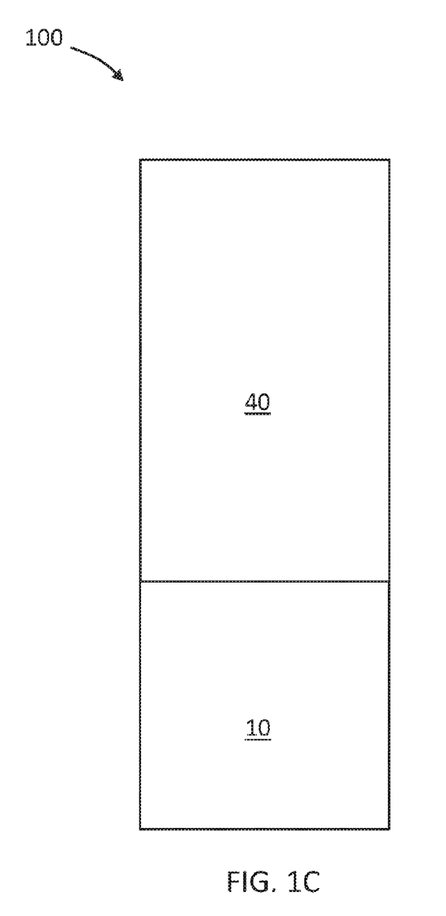
FIG. 1C is a plan view of connected parts showing only exterior portions of the cover and first part.

Referring now to FIGS. 1A-C, an aerosol-generating system 100 includes a first part 10, a second part 20, a third part 30, and a cover 40. The first part 10 is releasably connectable to the second part 20. The second part 20 is releasably connectable to the third part 30. The cover 40 is disposable over the second 20 and third 30 parts. The cover 40 is releasably securable in a position relative to the second 20 and third 30 parts.

The first part 10 comprises a housing 130 in which a power supply 110 and electronic circuitry 120 is disposed. The electronic circuitry 120 is electrically coupled to the power supply 110. Electrical conductors 140 may connect contacts (not shown) exposed through, positioned on, or formed from the housing 130.

The second part 20 comprises a housing 240 in which a liquid transfer element 210 and a heating element 220 are disposed. The liquid transfer element 210 is in thermal connection with the heating element 220. Electrical conductors 230 electrically couple the heating element 220 to electrical contacts (not shown) exposed through, positioned on, or formed from the housing 240. When the second part 20 is connected to the first part 10 (for example, as shown in FIG. 1B), the heating element 220 is electrically coupled with the circuitry 120 and power supply 110.

The third part 30 comprises a housing 310 defining a reservoir 300 in which a liquid aerosol generating substrate (not shown) is stored. When the third part 30 is connected to the second part 20, the reservoir 300 and thus the liquid aerosol generating substrate is in fluid communication with the liquid transfer element 210. The third part 30 may include valves 399 configured to be close when the second and third parts are not connected (such as in FIG. 1A) and configured to be open when the second and third parts are connected (such as in FIG. 1B). The valves 399 are aligned with distal openings in the third part 30 and proximal openings in the second part 20 such that when the valves are open, liquid aerosol generating substrate in the reservoir 300 is in communication with liquid transfer element 210.

The second part 20 includes proximal protruding elements 249 configured to be received in recesses 349 of the third part to securely couple the second and third parts. A mechanism (not shown) coupled to valve 349 may be positioned in one or more recesses 349 such that when protruding element 249 is inserted into recess 349, the valve 399 opens and when protruding element 249 is withdrawn from recess 349, the valve 399 closes.

Also shown in FIGS. 1A and 1B are passageways for air or aerosol flow through the system 100. The second part 20 comprises inlets in housing in communication with passageway 215 that extends to the proximal end of the second part. A central passageway 315 extends through the third part 30 and is in communication with the passageway 215 of the second part 20 when the second 20 and third 30 parts are connected. The cover 40 comprises a central passageway 415. The central passageway 415 of the cover 40 is in communication with the central passageway 315 of the third part 30 when the cover 40 is disposed over the third part 30.

In at least one example embodiment, as shown in FIGS. 1A-C, the cover 40 is configured to be disposed over the second 20 and third parts 30. In at least one example embodiment, a smooth transition is formed across the outer surface of the system 100 at the transition between the cover 40 and the first part 10. The cover 40 may be maintained in position in any suitable manner, such as such as threaded engagement, snap-fit engagement, interference-fit engagement, magnetic engagement, or the like to any one or more of the first part 10, second part 20, or third part 30 (engagement not shown).

Figure 2A:
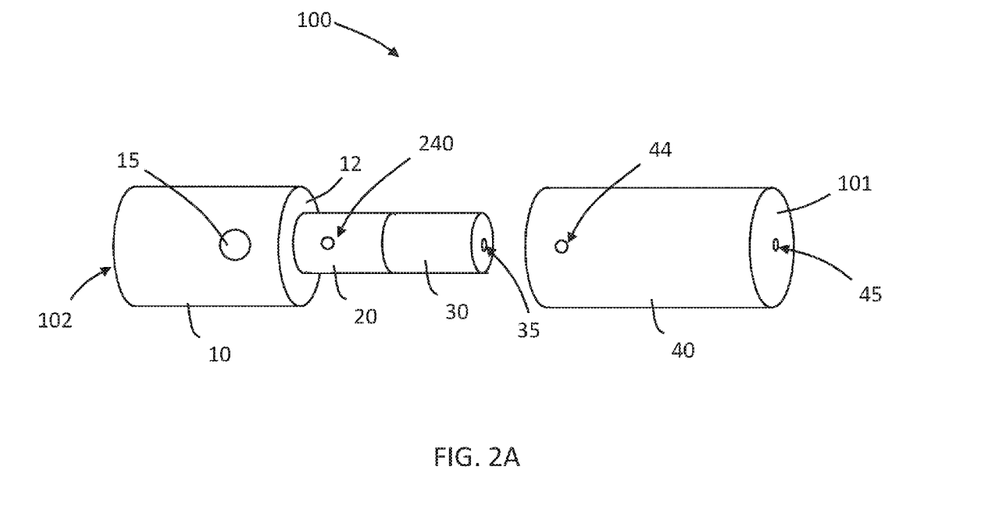
FIG. 2A shows the first, second and third parts connected and the cover removed.
Figure 2B:
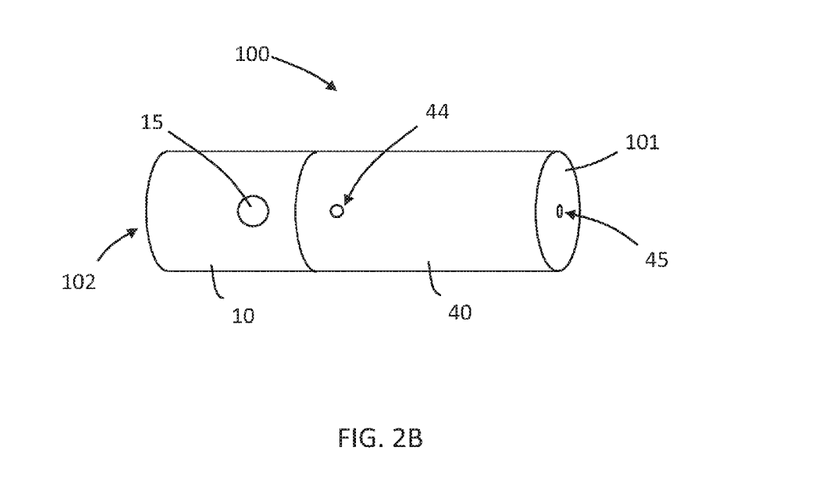
FIG. 2B shows the system with the cover secured in place about the second and third parts.

Referring now to FIGS. 2A-B, an aerosol-generating system 100 includes a first part 10, a second part 20, a third part 30 and a cover 40. The parts are generally as described with regard to FIGS. 1A-C. The connected system extends from a mouth end 101 to a distal end 102. The housing of the third part 30 (capsule) defines an opening 35 in communication with a passage through the third part 30. The passage defines a portion of an aerosol flow path through the system 100. The housing of the second part 20 (vaporizing unit) defines an air inlet 240 in communication with a passage through the second part 20. The passage through the second part 20 is in communication with the passage through the third part 30. The cover 40, which is configured to cover the second 20 and third parts 30, comprises a sidewall defining an air inlet 44 that is in communication with the air inlet 240 of the second part 20 when the cover 40 is secured in place relative to the other parts of the system. The housing of the cover 40 also defines a mouth end opening 45 that is in communication with the passage through the third part 30. Accordingly, when an adult vaper draws on the mouth end 101 of the system 100, air enters inlet 44 of cover 40, then enters inlet 240 of the vaporizing unit (second part 20), flows through the passage in the vaporizer unit, through the passage in the capsule (third part 30), through the opening 35 at the proximal end of the capsule, and through the mouth end opening 45.

The first part 10 of the aerosol-generating system depicted in FIGS. 2A-B includes a button 15 that may be depressed to activate, and optionally, to deactivate the system. The button 15 is coupled to a switch of the circuitry of the first part 10.

Also shown in the system 100 depicted in FIG. 2A, the housing of the first part 10 defines a rim 12 at the proximal end. The distal end of the cover 40 contacts the rim 12 when the cover 40 is secured in place over the second 20 and third 30 parts. In at least one example embodiment, the size and shape of the outer edge of the rim 12 of the housing of the first part 10 is substantially the same as the size and shape of the outer edge of the distal end of the cover 40 so that a smooth along the outer surface of the system is formed at the junction of the first part and the cover.

Figure 3:
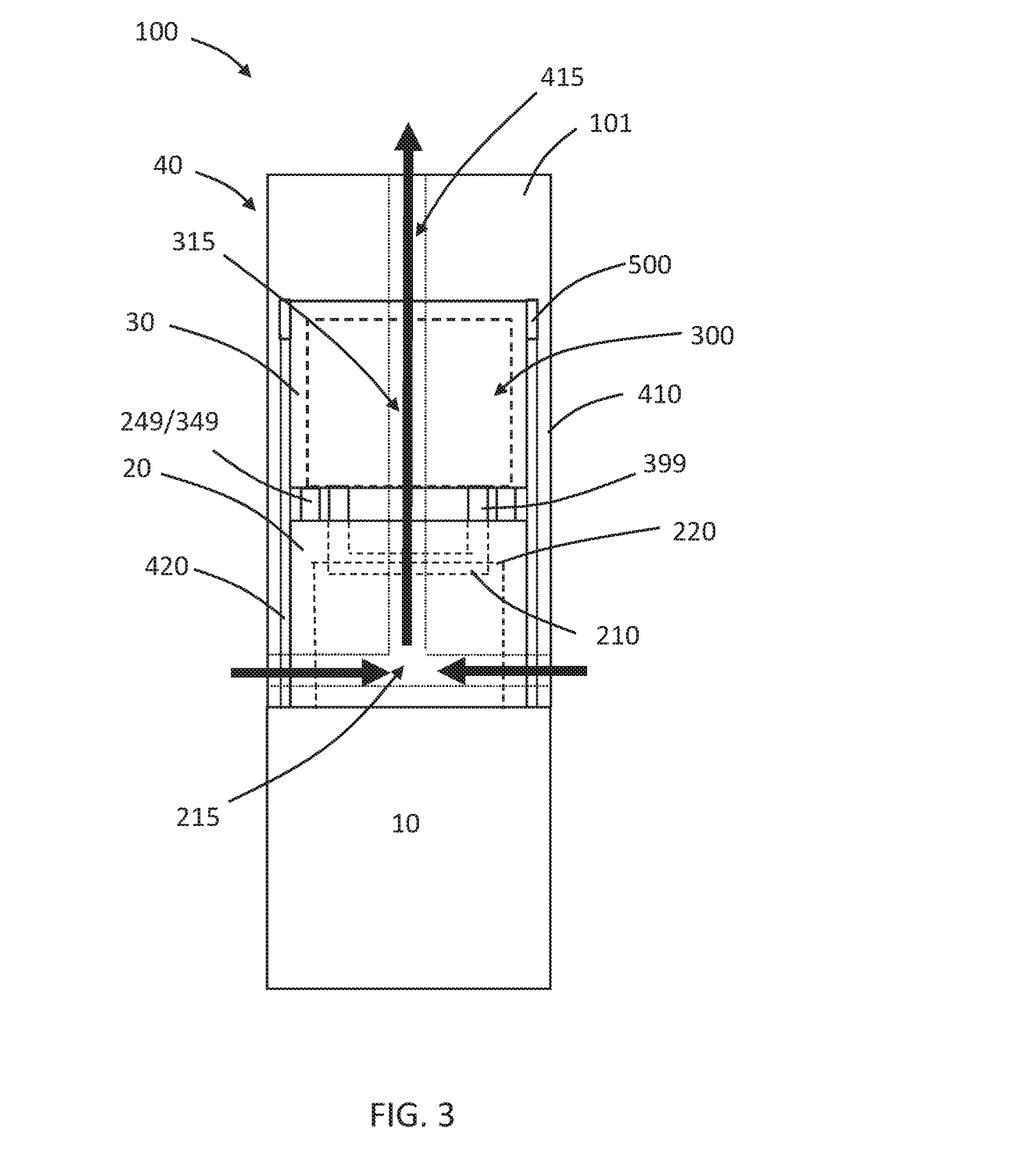
FIG. 3 is a schematic sectional view of an example of an aerosol-generating system having connected parts and cover, and illustrating an aerosol flow path.

Referring now to FIG. 3, an aerosol flow path through the system 100 is illustrated by thick arrows. As in FIGS. 1A-C and 2A-B, the system includes a first part 10, second part 20, third part 30, and cover 40 disposed over the second 20 and third 30 parts and in contact with a rim of the first part 10. When the parts of the system are connected, heating element 220 is coupled to control electronics and power supply (not shown) of first part, valves 399 are open to allow liquid aerosol generating substrate to flow to liquid transfer element 210. Valves 399 may be opened by interaction of protruding element 249 with mechanism (not shown) in recess 349. When an adult vaper draws on the mouth end 101, fresh air enters into the system through a sidewall 410 of the cover, such as through an air inlet 44 as depicted in FIG. 2A. The air may then flow into the second part 20 (vaporizing unit), such as through inlet 240 as depicted in FIG. 2A, and through a passage 215 in vaporizing unit with which liquid transfer element 210 is in communication. The liquid transfer element 210 which carries the aerosol generating substrate may be heated by heating element 220 to cause aerosol to be generated from the heated substrate. The aerosol may be entrained in the air, which flows through a passage 315 in the third part 30 (capsule), through a passage 415 in the cover, and out of the mouth end 101, such as through mouth end opening 45 as depicted in FIG. 2B. The depicted cover 40 includes a seal 500 to block flow of air around the second 20 and third 30 parts in the space 420 between the cover and the second 20 and third 30 parts and out of the mouth end 101. The seal 500 may engages an outer surface of the third part 30 and engage an inner surface of the cover 40 at a plane substantially transverse to the housing and may be disposed between the air inlets 44 and the mouth end 101 of the system. The seal 500 thus encourages air flow to follow the depicted aerosol flow path.

Figure 4A:
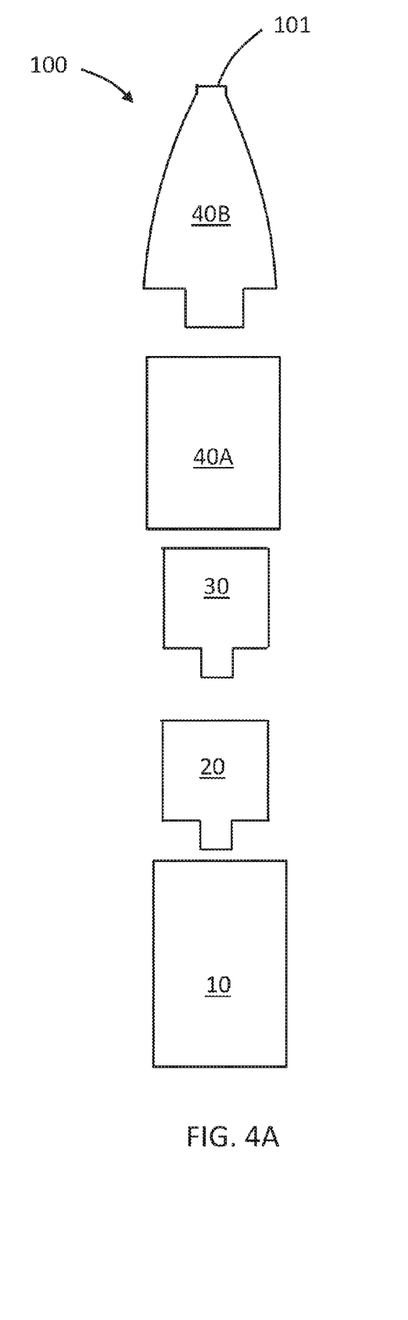
FIG. 4A shows the all parts disconnected.
Figure 4B:
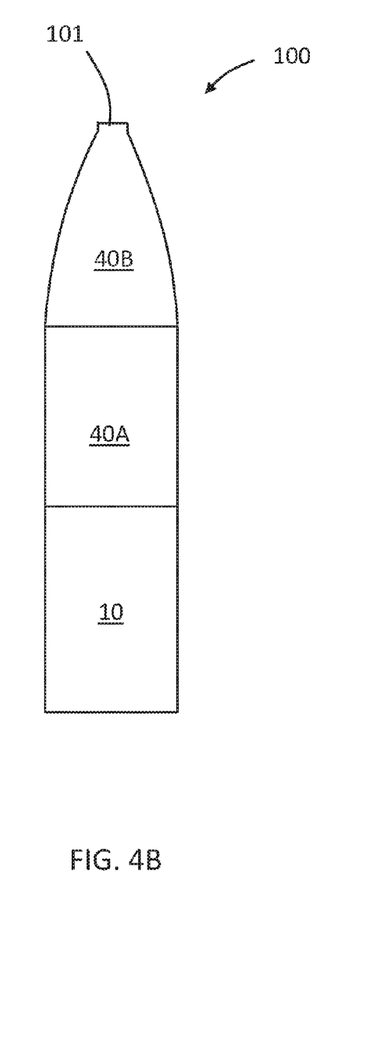
FIG. 4B shows all parts connected.
Figure 5A:
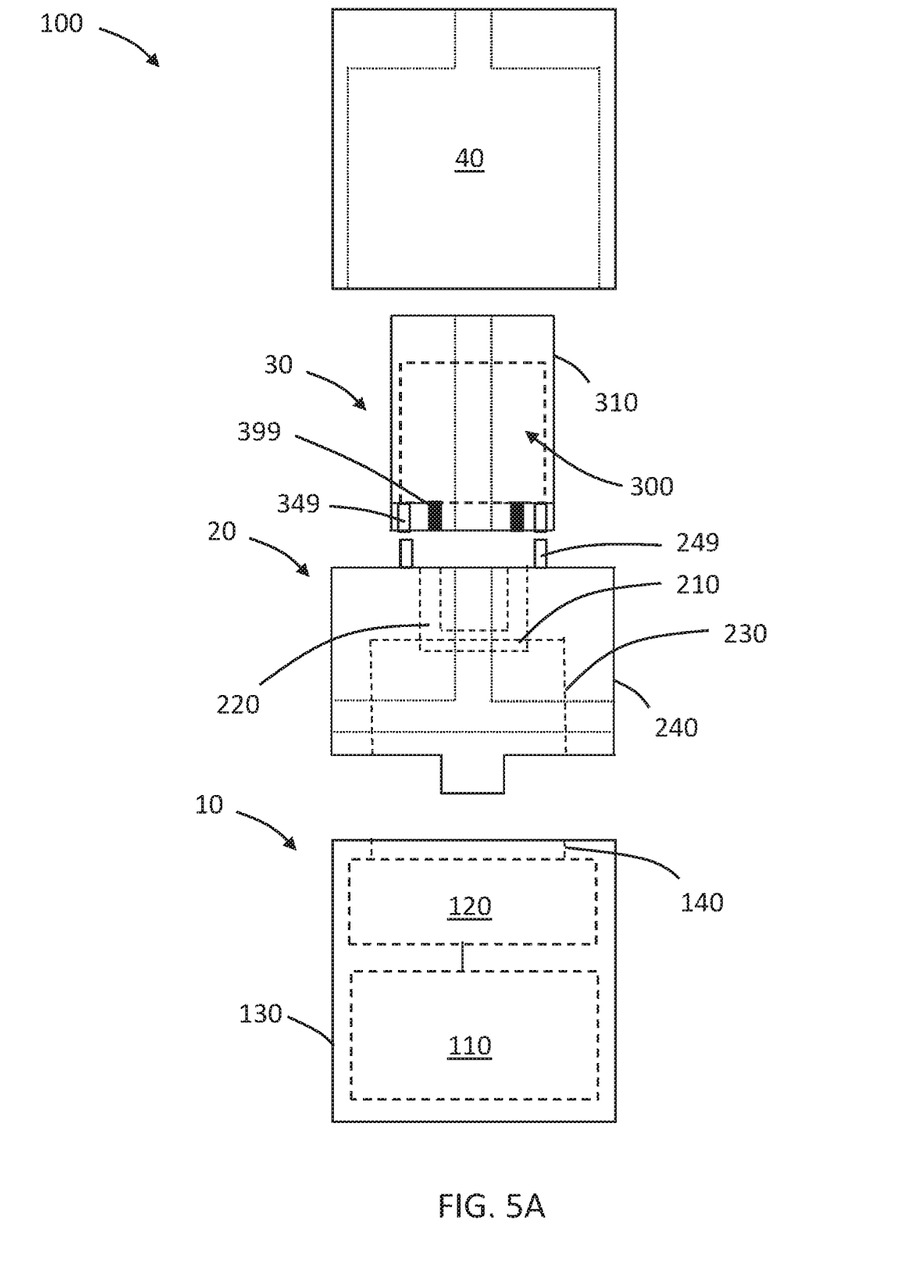
FIG. 5A is a plan view of disconnected first, second and third parts and cover, and illustrates some internal components of the parts.
Figure 5B:
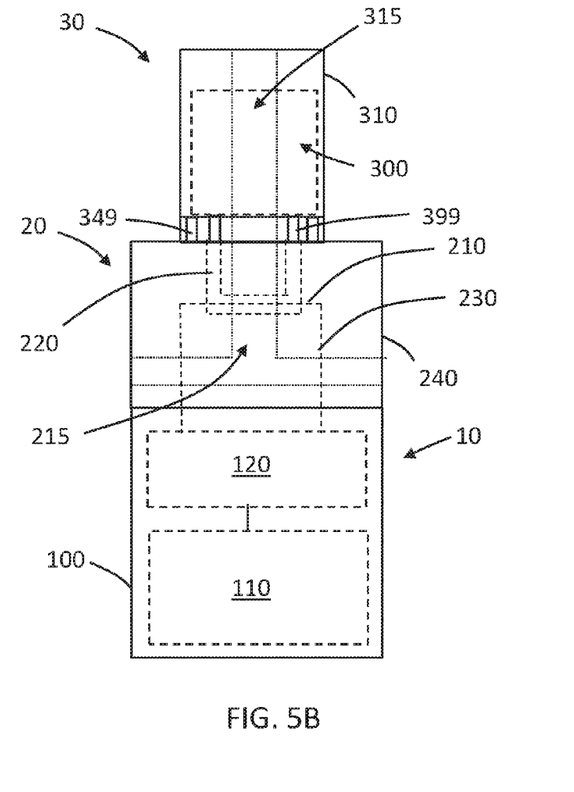
FIG. 5B is a plan view of connected first, second and third parts illustrating some internal components of the parts.
Figure 5C:
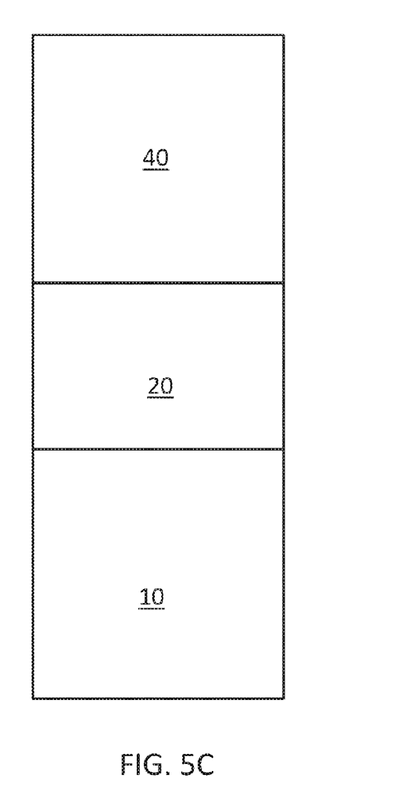
FIG. 5C is a plan view of connected parts showing only exterior portions of the cover and first part.
Figure 6A:
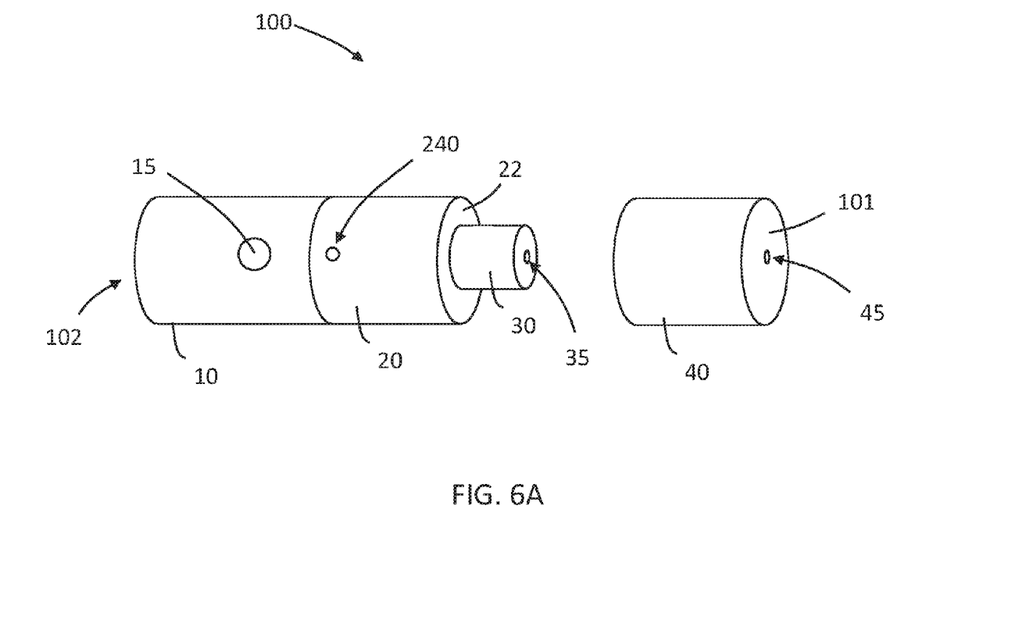
FIG. 6A shows the first, second and third parts connected and the cover removed.
Figure 6B:
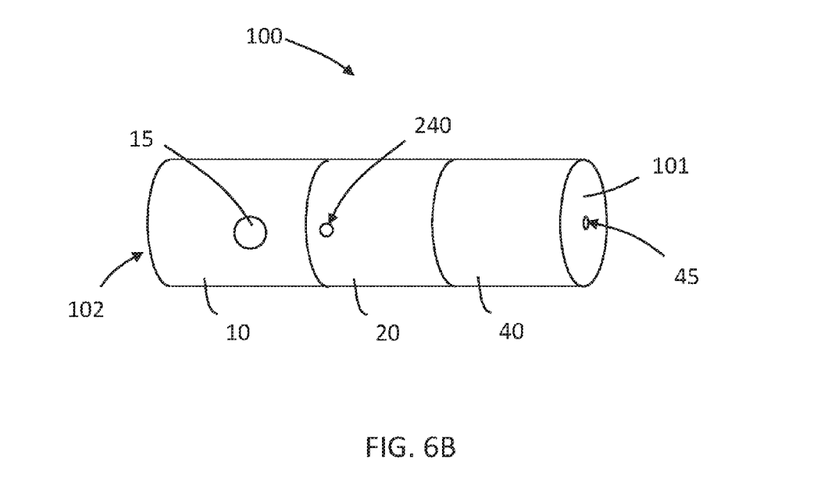
FIG. 6B shows the system with the cover secured in place about the second and third parts.

Referring now to FIGS. 4A-B, an aerosol-generating system 100 including a two-part 40A, 40B cover is shown. Cover part 40B serves as a mouthpiece and defines the mouth end 101 of the system 100. Cover part 40A and cover part 40B may be releasably connectable to one another. The depicted cover 40A, 40B is configured to cover the second 20 and third 30 parts and to abut a proximal end of the first part 10.

Referring now to FIGS. 5A-C and 6A-B, an aerosol-generating system 100 in which the cover 40 is configured to cover the third part 30, but not the second part 20, is shown. Many of the parts and components depicted in FIGS. 5A-C and 6A-B, are the same or similar to those depicted in, and described with regard to, FIGS. 1A-C and 2A-B. Reference is made to the discussion above regarding FIGS. 1A-C and 2A-B for numbered elements depicted in, but not specifically discussed with regard to, FIGS. 5A-C and 6A-B.

In the systems 100 depicted in FIGS. 5A-C and 6A-B, the distal end of the cover 40 engages a rim 22 on the proximal end of the housing of the second part 20. Because cover 40 does not cover the distal portion of the second part 20, the cover 40 does not block air inlets 240 and thus the cover 40 need not include air inlets.

Various modifications and variations of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the mechanical arts, electrical arts, and aerosol generating article manufacturing or related fields are intended to be within the scope of the following claims.

I claim:

1. A multi-part aerosol-generating system having a mouth end and a distal end, the system comprising:
   a first part including,
      a housing, and
      a power supply disposed in the housing;
   a second part releasably connectable with the first part, the second part including,
      a liquid transfer element, and
      a heating element, the heating element electrically coupled to the power supply when the second part is connected with the first part, the heating element configured to heat a liquid aerosol generating substrate transferred by the liquid transfer element;
   a third part releasably connectable with the second part, the third part including,
      a reservoir containing the liquid aerosol generating substrate, the liquid aerosol generating substrate in fluid communication with the liquid transfer element when the third part is connected with the second part; and
   a cover disposable over the third part, the cover releasably securable in a position relative to the third part, and the cover defining the mouth end of the system, the cover including a mouthpiece defining the mouth end of the system, the mouthpiece configured to sealingly engage an inner surface of the cover and an outer surface of the housing of the third part.

2. The multi-part aerosol-generating system according to claim 1, wherein the second part has a proximal end and a distal end with respect to the mouth end of the system,
   wherein the proximal end of the second part defines a rim defining an outer edge,
   wherein the cover comprises a proximal end and a distal end with respect to the mouth end of the system,
   wherein the distal end of the cover defines an outer edge and defines an opening through which the third part is receivable, and
   wherein the distal end of the cover abuts the proximal end rim of the second part when the cover is secured in the position relative to the third part.

3. The multi-part aerosol-generating system according to claim 1, wherein the cover is disposable over the second and third parts.

4. The multi-part aerosol-generating system according to claim 2, wherein the first part has a proximal end and a distal end with respect to the mouth end of the system,
   wherein the proximal end of the first part defines a rim defining an outer edge,
   wherein the cover comprises a proximal end and a distal end with respect to the mouth end of the system, wherein the distal end of the cover defines an outer edge and defines an opening through which the second and third parts are receivable, and wherein the distal end of the cover abuts the proximal end rim of the housing of the first part when the cover is secured in the position relative to the third part.

5. The multi-part aerosol-generating system according to claim 4, wherein the outer edge of the rim of the housing of the first part has a size and shape, and wherein the outer edge of the distal end of the cover has a size and shape substantially the same as the size and shape of the outer edge of the rim of the housing of the first part.

6. The multi-part aerosol-generating system according to claim 1, wherein the cover comprises a sidewall and one or more air inlets extending through the sidewall, wherein the air inlets are in proximity to the distal end of the cover.

7. The multi-part aerosol-generating system according to claim 1, further comprising:
a seal configured to engage an outer surface of the third part and an inner surface of the cover at a plane substantially transverse to the housing, the seal between air inlets and the mouth end of the system.

8. A multi-part aerosol-generating system having a mouth end and a distal end, the system comprising:
a first part including,
a housing, and
a power supply disposed in the housing;
a second part releasably connectable with the first part, the second part including,
a liquid transfer element, and
a heating element, the heating element electrically coupled to the power supply when the second part is connected with the first part, the second part having a proximal end and a distal end with respect to the mouth end of the system, the proximal end of the second part defining a rim, the rim defining an outer edge, the heating element configured to heat a liquid aerosol generating substrate transferred by the liquid transfer element;
a third part releasably connectable with the second part, the third part including,
a reservoir containing the liquid aerosol generating substrate, the liquid aerosol generating substrate in fluid communication with the liquid transfer element when the third part is connected with the second part; and
a cover disposable over the third part, the cover releasably securable in a position relative to the third part, and the cover defining the mouth end of the system, the cover having a proximal end and a distal end with respect to the mouth end of the system, the distal end of the cover defining an outer edge and defining an opening through which the third part is receivable, and the distal end of the cover configured to abut the proximal end rim of the second part when the cover is secured in the position relative to the third part.

9. A multi-part aerosol-generating system having a mouth end and a distal end, the system comprising:
a first part including,
a housing, and
a power supply disposed in the housing;
a second part releasably connectable with the first part, the second part including,
a liquid transfer element, and
a heating element, the heating element electrically coupled to the power supply when the second part is connected with the first part, the heating element configured to heat a liquid aerosol generating substrate transferred by the liquid transfer element;
a third part releasably connectable with the second part, the third part including,
a reservoir containing the liquid aerosol generating substrate, the liquid aerosol generating substrate in fluid communication with the liquid transfer element when the third part is connected with the second part;
a cover disposable over the third part, the cover releasably securable in a position relative to the third part, and the cover defining the mouth end of the system; and
a seal configured to engage an outer surface of the third part and an inner surface of the cover at a plane substantially transverse to the housing, the seal between air inlets and the mouth end of the system.

10. The multi-part aerosol-generating system according to claim 1, wherein the cover comprises first and second releasably connectable parts, and the first part comprises the mouthpiece.

11. The multi-part aerosol-generating system according to claim 1, wherein the system defines a flow path through a passage that extends through at least a portion of the second part and through a passage that extends through the third part to the mouth end of the system.

12. The multi-part aerosol-generating system according to claim 1, wherein the cover is generally cylindrical in shape and tapers inwardly towards the mouth end.

13. The multi-part aerosol-generating system according to claim 1, wherein the third part comprises a valve actuable between (a) an open position to allow transfer of the liquid aerosol generating substrate from the reservoir to the liquid transfer element and (b) a closed position to prevent the liquid aerosol generating substrate from exiting the reservoir.

14. The multi-part aerosol-generating system according to claim 13, wherein the second and third parts are configured such that connecting the second and third parts causes the valve to adopt the open position and disconnecting the second and third parts causes the valve to adopt the closed position.

15. The multi-part aerosol-generating system according to claim 1, wherein the liquid aerosol generating substrate in the reservoir comprises free liquid, wherein the free liquid is in direct communication with the liquid transfer element when the second and third parts are connected.

* * * * *